(12) United States Patent
Towse et al.

(10) Patent No.: US 8,033,826 B2
(45) Date of Patent: Oct. 11, 2011

(54) TWO-PIECE DENTAL ABUTMENT SYSTEM

(75) Inventors: Ross W. Towse, Palm City, FL (US);
John J. Bellanca, Port St. Lucie, FL (US); Theodore M. Powell, Lake in The Hills, IL (US); Ralph E. Goodman, West Palm Beach, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 261 days.

(21) Appl. No.: 12/263,798

(22) Filed: Nov. 3, 2008

(65) Prior Publication Data
US 2009/0130629 A1     May 21, 2009

Related U.S. Application Data

(60) Provisional application No. 61/003,200, filed on Nov. 15, 2007.

(51) Int. Cl.
*A61C 8/00* (2006.01)
(52) U.S. Cl. .......................................... 433/172; 433/173
(58) Field of Classification Search .......... 433/172–176, 433/201.1
See application file for complete search history.

(56) References Cited

U.S. PATENT DOCUMENTS

| | | | |
|---|---|---|---|
| 2,721,387 A | 10/1955 | Ashuckian | |
| 3,958,471 A | 5/1976 | Muller | |
| 4,011,602 A | 3/1977 | Rybicki et al. | |
| 4,177,562 A | 12/1979 | Miller et al. | |
| 4,259,072 A | 3/1981 | Hirabayashi et al. | |
| 4,547,157 A | 10/1985 | Driskell | |
| 4,560,353 A | 12/1985 | Schulte et al. | |
| 4,575,340 A | 3/1986 | Lustig | |
| 4,624,673 A | 11/1986 | Meyer | |
| 4,713,004 A | 12/1987 | Linkow et al. | |
| 4,738,623 A | 4/1988 | Driskell | |
| 4,746,293 A | 5/1988 | Lundgren et al. | |
| 4,758,161 A | 7/1988 | Niznick | |
| 4,772,204 A | 9/1988 | Soderberg | |
| 4,824,372 A | 4/1989 | Jorneus et al. | |
| 4,846,683 A | 7/1989 | Lazzara et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |

(Continued)

FOREIGN PATENT DOCUMENTS

DE        21 14 323        10/1971

(Continued)

*Primary Examiner* — John J Wilson
(74) *Attorney, Agent, or Firm* — Nixon Peabody LLP

(57) ABSTRACT

The present inventions is an abutment for use with a dental implant. The abutment comprises a prosthetic portion adapted to support a prosthesis thereon and an insert. The prosthetic portion has a subgingival end and a supragingival region for protruding beyond gingiva adjacent to the dental implant. The prosthetic portion has a passageway extending therethrough. The passageway includes an enlarged retention groove and non-round section. The insert extends into the passageway and engages the subgingival end of the prosthetic portion. The insert includes flexible retention fingers that, upon insertion into the passageway, initially contract before reaching the enlarged retention groove and then expand outwardly into the enlarged retention groove to hold the insert onto the prosthetic portion. The insert also has a non-round section for mating with the non-round section of the passageway.

20 Claims, 9 Drawing Sheets

U.S. PATENT DOCUMENTS

| | | |
|---|---|---|
| 4,872,839 A | 10/1989 | Brajnovic |
| 4,904,187 A | 2/1990 | Zingheim |
| 4,955,811 A | 9/1990 | Lazzara et al. |
| 4,978,640 A | 12/1990 | Kelly |
| 4,988,297 A | 1/1991 | Lazzara et al. |
| 4,988,298 A | 1/1991 | Lazzara et al. |
| 5,000,686 A | 3/1991 | Lazzara et al. |
| 5,006,069 A | 4/1991 | Lazzara et al. |
| 5,015,186 A | 5/1991 | Detsch |
| 5,022,860 A | 6/1991 | Lazzara et al. |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,373 A | 11/1991 | Staubli et al. |
| 5,071,345 A | 12/1991 | Rosen |
| 5,071,351 A | 12/1991 | Green, Jr. et al. |
| 5,073,111 A | 12/1991 | Daftary |
| 5,082,442 A | 1/1992 | Rosen |
| 5,087,200 A | 2/1992 | Brajnovic et al. |
| 5,100,323 A | 3/1992 | Friedman et al. |
| 5,104,318 A | 4/1992 | Piche et al. |
| 5,105,690 A | 4/1992 | Lazzara et al. |
| 5,106,300 A | 4/1992 | Voitik |
| 5,122,059 A | 6/1992 | Durr et al. |
| 5,125,839 A | 6/1992 | Ingber et al. |
| 5,135,395 A | 8/1992 | Marlin |
| 5,145,371 A | 9/1992 | Jorneus |
| 5,145,372 A | 9/1992 | Daftary et al. |
| 5,152,687 A | 10/1992 | Amino |
| 5,154,612 A | 10/1992 | Carlsson et al. |
| 5,169,308 A | 12/1992 | Kvist |
| 5,169,309 A | 12/1992 | Staubli et al. |
| 5,188,800 A | 2/1993 | Green, Jr. et al. |
| 5,195,891 A * | 3/1993 | Sulc .................... 433/173 |
| 5,195,892 A | 3/1993 | Gersberg |
| 5,197,881 A | 3/1993 | Chalifoux |
| 5,209,659 A | 5/1993 | Friedman et al. |
| 5,209,666 A | 5/1993 | Balfour et al. |
| 5,213,502 A | 5/1993 | Daftary |
| 5,246,370 A | 9/1993 | Coatoam |
| 5,281,140 A | 1/1994 | Niznick |
| 5,282,746 A | 2/1994 | Sellers et al. |
| 5,286,195 A | 2/1994 | Clostermann |
| 5,292,252 A | 3/1994 | Nickerson et al. |
| 5,297,963 A | 3/1994 | Daftary |
| 5,316,476 A | 5/1994 | Krauser |
| 5,334,024 A | 8/1994 | Niznick |
| 5,336,090 A | 8/1994 | Wilson, Jr. et al. |
| 5,338,196 A | 8/1994 | Beaty et al. |
| 5,344,457 A | 9/1994 | Pilliar et al. |
| 5,350,300 A | 9/1994 | Gallais |
| 5,362,234 A | 11/1994 | Salazar et al. |
| 5,362,235 A | 11/1994 | Daftary |
| 5,368,483 A | 11/1994 | Sutter et al. |
| 5,417,570 A | 5/1995 | Zuest et al. |
| 5,419,702 A | 5/1995 | Beaty et al. |
| 5,431,567 A | 7/1995 | Daftary |
| 5,433,606 A | 7/1995 | Niznick et al. |
| 5,437,551 A | 8/1995 | Chalifoux |
| 5,447,435 A | 9/1995 | Brodbeck |
| 5,476,382 A | 12/1995 | Daftary |
| 5,476,383 A | 12/1995 | Beaty et al. |
| 5,492,471 A | 2/1996 | Singer |
| 5,533,898 A | 7/1996 | Mena |
| 5,538,426 A | 7/1996 | Harding et al. |
| 5,547,377 A | 8/1996 | Daftary |
| 5,564,924 A | 10/1996 | Kwan |
| 5,571,016 A | 11/1996 | Ingber et al. |
| 5,588,838 A | 12/1996 | Hansson et al. |
| 5,662,473 A * | 9/1997 | Rassoli et al. ................ 433/172 |
| 5,685,714 A | 11/1997 | Beaty et al. |
| 5,699,148 A | 12/1997 | Shiozawa |
| 5,777,724 A | 7/1998 | Suzuki |
| 5,782,918 A * | 7/1998 | Klardie et al. .................. 606/60 |
| 5,816,812 A * | 10/1998 | Kownacki et al. ............. 433/174 |
| 5,829,977 A | 11/1998 | Rogers et al. |
| 5,989,026 A | 11/1999 | Rogers et al. |
| 6,152,737 A | 11/2000 | Beaty et al. |
| 6,168,435 B1 | 1/2001 | Beaty et al. |
| RE37,227 E | 6/2001 | Brodbeck |
| 2004/0101808 A1 * | 5/2004 | Porter et al. .................. 433/173 |

FOREIGN PATENT DOCUMENTS

| | | |
|---|---|---|
| DE | 21 57 139 | 5/1972 |
| DE | 27 17 506 | 5/1978 |
| DE | 32 24 112 A1 | 2/1984 |
| DE | 35 31 389 A1 | 3/1987 |
| DE | 38 25 601 A1 | 3/1989 |
| DE | 40 28 855 A1 | 3/1992 |
| DE | 41 27 839 A1 | 3/1992 |
| EP | 0 320 024 A1 | 6/1989 |
| EP | 0 477 644 A1 | 4/1992 |
| EP | 0 657 146 A1 | 6/1995 |
| GB | 1 291 470 | 10/1972 |
| GB | 2 213 065 | 8/1989 |
| SU | 1570720 A1 | 6/1990 |
| WO | WO 85/02337 A1 | 6/1985 |

* cited by examiner

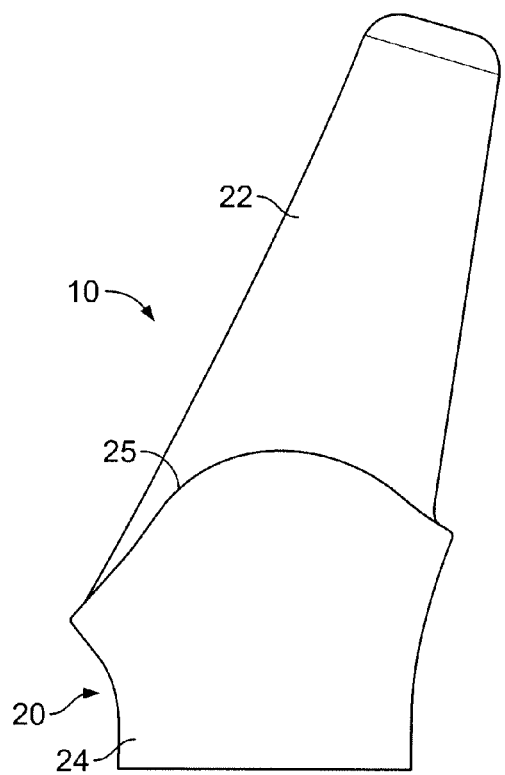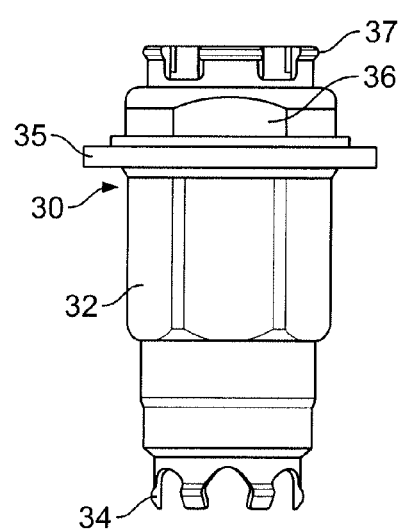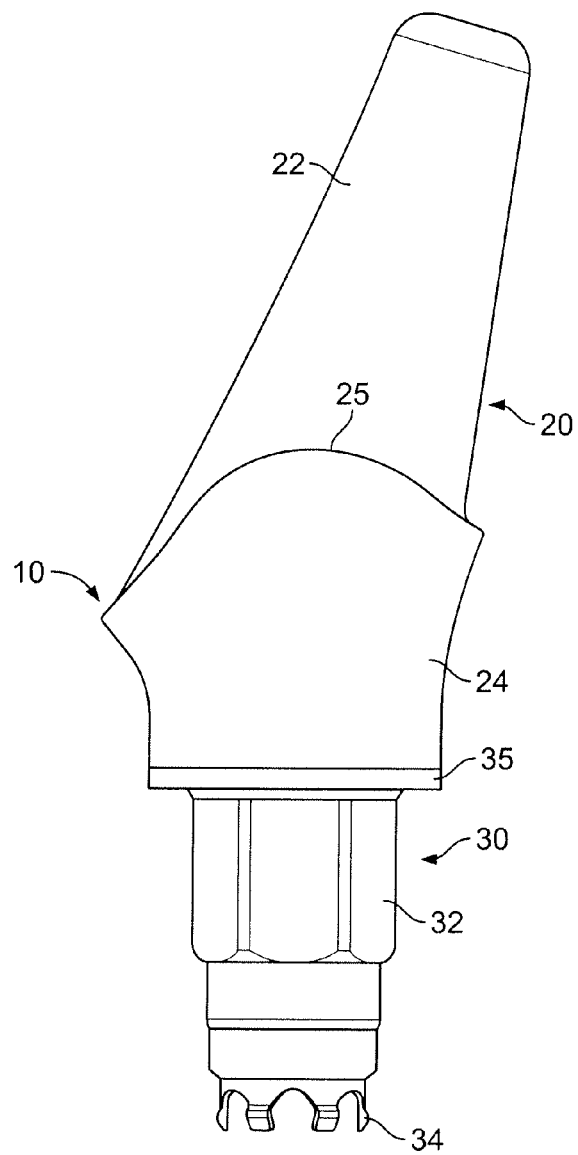
FIG. 1A      FIG. 1B

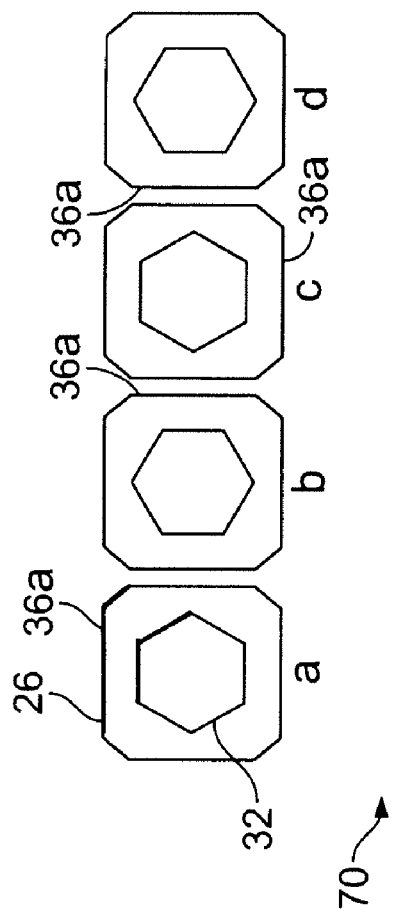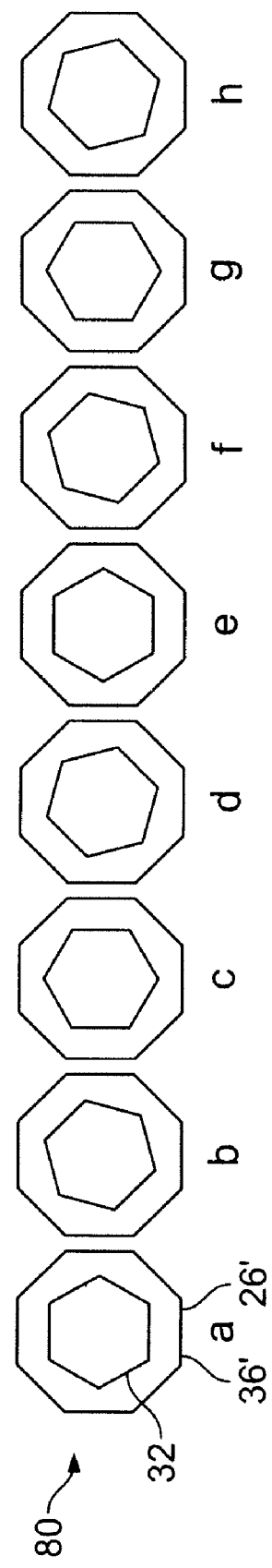
FIG. 7A
FIG. 7B

TWO-PIECE DENTAL ABUTMENT SYSTEM

CROSS REFERENCE TO RELATED APPLICATION

This application claims the benefit of the U.S. Provisional Application No. 61/003,200, filed on Nov. 15, 2007, which is hereby incorporated by reference in its entirety.

FIELD OF INVENTION

The present invention relates generally to dental implant systems. More particularly, the present invention relates to a two-piece abutment system.

BACKGROUND OF THE INVENTION

The dental restoration of a partially or wholly edentulous patient with artificial dentition is typically done in two stages. In the first stage, an incision is made through the gingiva to expose the underlying bone. After a series of drill bits creates an osteotomy in the bone, a dental implant is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant preferably has the same general contour as the gingival portion of the natural tooth being replaced.

Once the clinician believes the implant is suitable for receiving a prosthesis, surgical techniques are used to place the dental prostheses by means of an abutment, which is often metallic. According to one prior art technique, the metallic abutment has an internally shouldered access bore through which a screw is inserted to hold the abutment on the implant.

In other techniques, a ceramic abutment is used. Since a ceramic support post is of greater hardness than a titanium implant, the ceramic may cause damage to the implant. In some embodiments, a metal core is used with a ceramic post to allow for a titanium-to-titanium interface between the abutment and the implant. Further, when examining the juncture between the support abutment and the titanium implant through conventional dental x-ray imaging, the interface between the metallic core and the implant is more readily viewable. Such embodiments of a ceramic abutment with a metallic core are shown, for example, in U.S. Pat. Nos. 6,343,930 and 6,168,435, which are commonly assigned and herein incorporated by reference in their entireties.

SUMMARY OF THE INVENTION

In one aspect, the invention is an abutment for use with a dental implant having an internally threaded bore and a non-round fitting located at a gingival end portion thereof. The abutment comprises a prosthetic portion, an insert, and a screw. The prosthetic portion is adapted to support a prosthesis thereon. The prosthetic portion has a supragingival region for protruding beyond gingiva adjacent to the dental implant and a subgingival end. The prosthetic portion has a passageway extending therethrough. The passageway includes an enlarged retention groove and a narrow shoulder. The insert extends into the passageway and engages the subgingival end of the prosthetic portion. The insert has a central opening and an anti-rotational feature for engaging the non-round fitting of the dental implant. The insert includes flexible retention fingers that, upon insertion into the passageway, initially contract before reaching the enlarged retention groove and then expand outwardly into the enlarged retention groove to hold the insert onto the prosthetic portion. The screw is adapted to engage threads of the internally threaded bore in the implant. The screw is insertable through the passageway in the prosthetic portion and the central opening in the insert. The screw comprises a head and a threaded section. The head of the screw seats on the shoulder in the passageway.

In another aspect, the present invention is a method of manufacturing a dental abutment for use on a dental implant in a patient's mouth. The dental abutment has an insert and a prosthetic portion. The method comprises (i) placing an upper segment of the insert into a passageway of the prosthetic portion, and (ii) in response to the insert being placed a certain distance within the passageway, snap-fitting the insert into a final position with the prosthetic portion.

In a further aspect, the present invention is a kit of components for creating an abutment for use with a dental implant having a non-round fitting located at a gingival end portion thereof. The kit comprises a first prosthetic portion having a first shape and being made of a first material and a second prosthetic portion having a second shape different from the first shape and being made of a second material that is different from the first material. The kit further comprises an insert that is extendable into either of the first prosthetic portion and the second prosthetic portion. The insert includes an anti-rotational feature for mating with the non-round fitting of the implant.

In a further aspect, the present invention is an abutment for use with a dental implant. The dental implant has an internally threaded bore and a non-round fitting located at a gingival end portion thereof. The abutment comprises a prosthetic portion adapted to support a prosthesis thereon and an insert. The prosthetic portion has a subgingival end and a supragingival region for protruding beyond gingiva adjacent to the dental implant. The supragingival region is asymmetrically arranged around a central axis of the prosthetic portion such that the abutment can function as an angled abutment. The prosthetic portion has a passageway extending therethrough. The passageway includes an enlarged retention groove and non-round section having "n" number of sides. The insert extends into the passageway and engages the subgingival end of the prosthetic portion. The insert has a central opening and an anti-rotational feature with "m" sides for engaging the non-round fitting of the dental implant. The insert includes flexible retention fingers that, upon insertion into the passageway, initially contract before reaching the enlarged retention groove and then expand outwardly into the enlarged retention groove to hold the insert onto the prosthetic portion. The insert includes a corresponding non-round section with "n" number of sides for mating with the non-round section of the passageway. The insert is insertable into the prosthetic portion in one of a plurality of positions such that the asymmetrically arranged supragingival region can be at one of a plurality of angles with respect to one of the "m" sides on the anti-rotational feature.

In yet another aspect, the present invention is an abutment for use with a dental implant. The dental implant has an internally threaded bore and a non-round fitting located at a gingival end portion thereof. The abutment comprises a prosthetic portion adapted to support a prosthesis thereon and an insert. The prosthetic portion has a subgingival end and a supragingival region for protruding beyond gingiva adjacent to the dental implant. The supragingival region is asymmetrically arranged around a central axis of the prosthetic portion such that the abutment can function as an angled abutment. The prosthetic portion has a passageway extending therethrough. The passageway includes a non-round section having "n" number of sides. The insert extends into the passageway and engages the subgingival end of the prosthetic portion. The insert has a central opening and an anti-rotational feature with "m" sides for engaging the non-round fitting of the dental implant. The insert includes a corresponding non-round section with "n" number of sides for mating with the non-round section of the passageway. The number "n" is different from the number "m". The insert is insertable into the prosthetic portion in one of a plurality of positions such that the asymmetrically arranged supragingival region can be at one of a plurality of angles with respect to one of the "m" sides on the anti-rotational feature.

BRIEF DESCRIPTION OF THE DRAWINGS

FIGS. 1A and 1B illustrates a two-piece abutment including a prosthetic portion and an insert;

FIGS. 7A and 7B illustrate the possible anti-rotational orientations for two differently manufactured two-piece abutments relative to the hexagonal fitting of the implant;

Figure 2A:
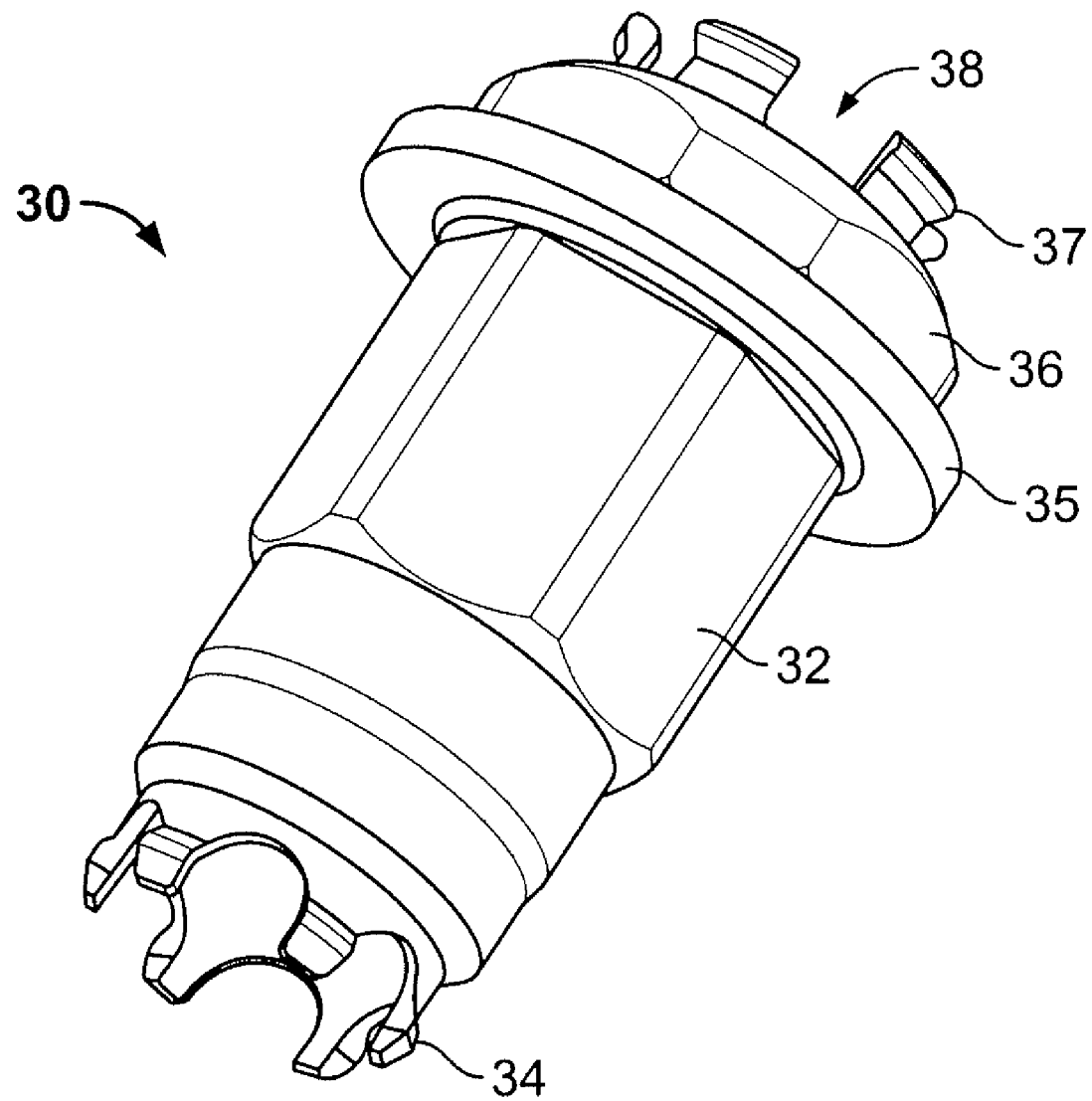
FIGS. 2A-2C illustrate the details of the insert in FIG. 1.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

FIGS. 1A and 1B illustrate a two-piece abutment 10, which includes a prosthetic portion 20 and an insert 30. The prosthetic portion 20 includes a support region 22 and a subgingival region 24. The support region 22 and the subgingival region 24 are separated by a shoulder 25. In operation, toothlike material, such as porcelain, is formed into the size and shape of a natural tooth and is mounted on the support region 22, interfacing at the shoulder 25. The shoulder 25 is typically just below the gingival tissue.

The insert 30 includes an anti-rotational feature 32 (e.g., a hexagonally shaped region) and an axial engagement section 34. The axial engagement section 34 comprises a plurality of prongs that snap outwardly into a corresponding feature within an internal bore of an implant to hold the two-piece abutment 10 on the implant.

The insert 30 further includes a table 35 that interfaces with the prosthetic portion 20, as shown best in FIG. 1B. Above the table 35, there is a non-round section 36 and a plurality of resilient fingers 37 that are separated by slots. As will be described in more detail with reference to FIG. 4, the plurality of resilient fingers 37 serves to axially hold the insert 30 on the prosthetic portion 20. Further, the non-round section 36 serves to non-rotationally hold the insert 30 within the prosthetic portion 20.

Figure 2B:
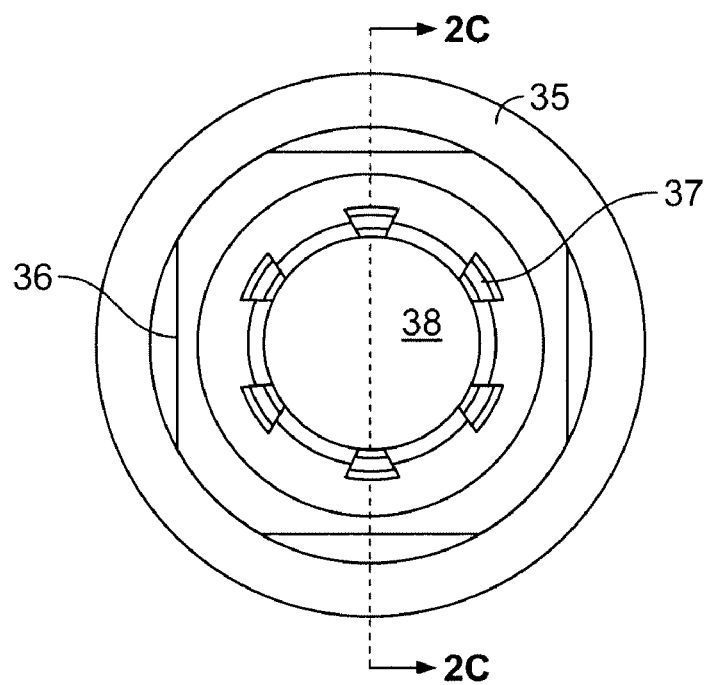
Figure 2C:
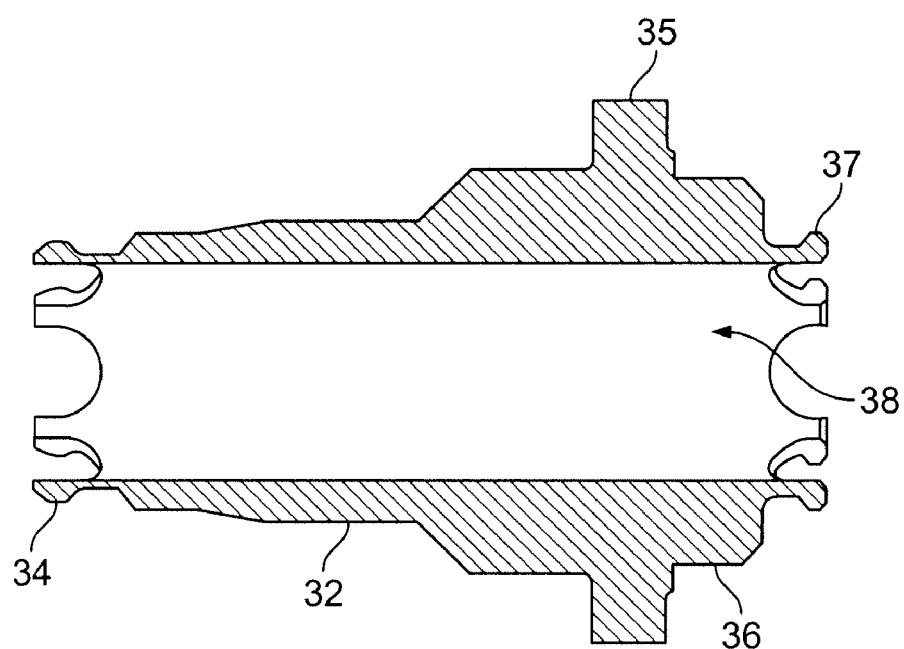

As shown in FIGS. 2A-2C, the insert 30 generally has a tubular shape due to an internal opening 38 that extends entirely through the insert 30. The upper portion above the table 35 is for engaging the prosthetic portion 20. The lower portion below the table 35 is for engaging the implant. In the illustrated embodiment, two opposing surfaces of the non-round section 36 are substantially aligned with two opposing surfaces of the anti-rotational feature 32 as shown in FIG. 2A. However, this is not required as these surfaces can be angularly offset from each other.

Figure 3A:
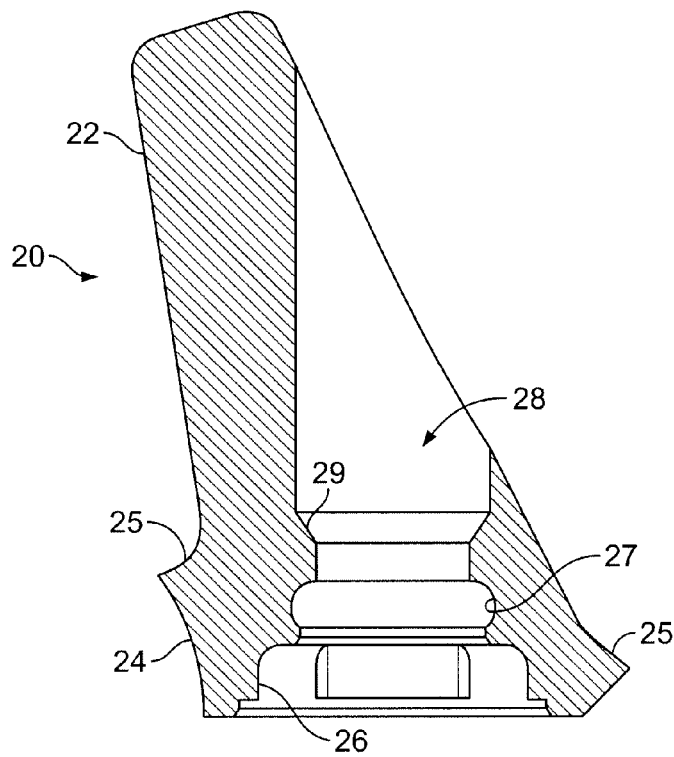
FIGS. 3A-3B illustrate the details of the prosthetic portion of FIG. 1.
Figure 3B:
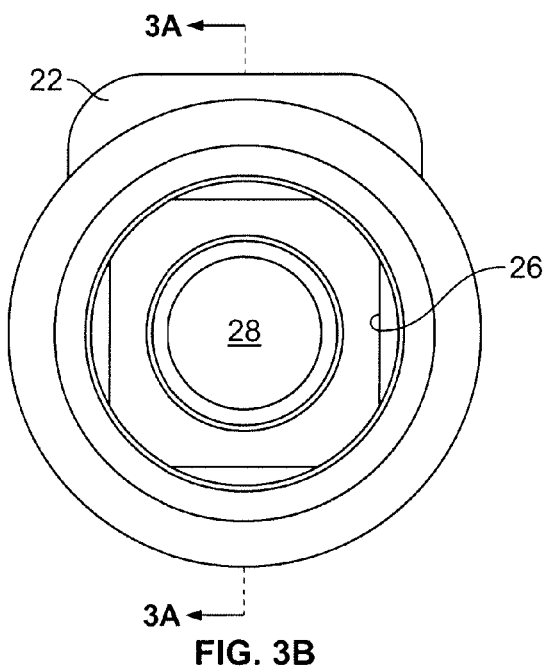

FIGS. 3A-3B illustrate the details of the prosthetic portion 20. In addition to the support region 22 and the subgingival region 24 on its exterior, the interior of the prosthetic portion 20 includes a non-round section 26 and an enlarged groove 27 within the internal bore 28. The support region 22 is asymmetrically arranged around a central axis of the prosthetic portion 20 such that the two-piece abutment 10 can be used as an angled abutment. In practice, the angle and distance at which the supporting region 22 extends from the central axis is varied in a kit of components such that a two-piece abutment 10 can be selected by the clinician so as to best fit the prevailing conditions in the patient's mouth.

Figure 4:
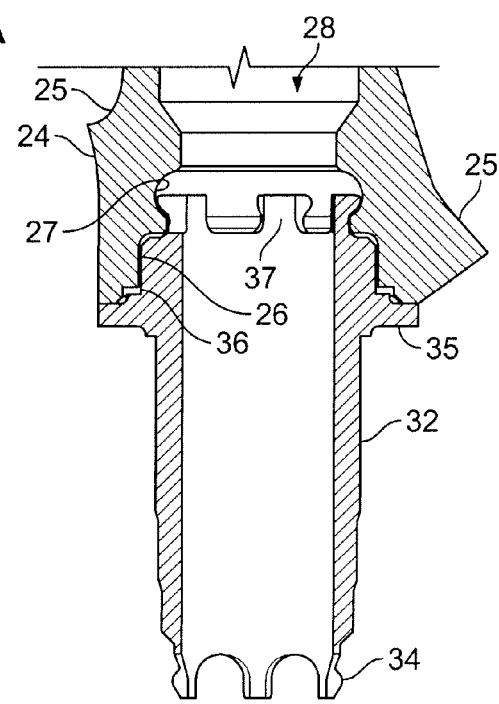
FIG. 4 illustrates the snap-fit, anti-rotational engagement between the prosthetic portion and the insert in FIG. 1.

FIG. 4 illustrates the engagement between the insert 30 and the prosthetic portion 20. As shown, the non-round section 26 of the prosthetic portion 20 and the non-round section 36 of the insert 30 non-rotationally engage to resist any rotational movement between the two parts. The non-round section 26 can be manufactured in various shapes and forms, and can be created by tools such as a D-broach, a square broach, or an octagonal broach.

Further, upon insertion of the plurality of fingers 37 into a known distance within the internal bore 28 of the prosthetic portion 20, the plurality of fingers 37 initially move inwardly and then snap outwardly into the enlarged groove 27 of the prosthetic portion 20. This snap-fit engagement is designed within enough strength such that the insert 30 and the prosthetic portion 20 remain attached without the assistance of any type of glue, cement, or sealing glass. However, the snap-fit engagement is reversible in that the insert 30 can be removed from the prosthetic portion 20. As an example, a tool may be insertable from the top into the internal bore 28 so as to engage a radially inner portion of the plurality of fingers 37, causing them to deform inwardly and be released from the enlarged groove 27.

The internal bore 28 further includes an angled surface 29 that meets with the head of a screw (FIG. 6) to hold the two-piece abutment 10 on the implant. The table 35 of the insert 30 substantially matches the dimension of the lowermost portion of the prosthetic portion 20 such that there is no overhang between the prosthetic portion 20 and the insert 30.

Figure 5:
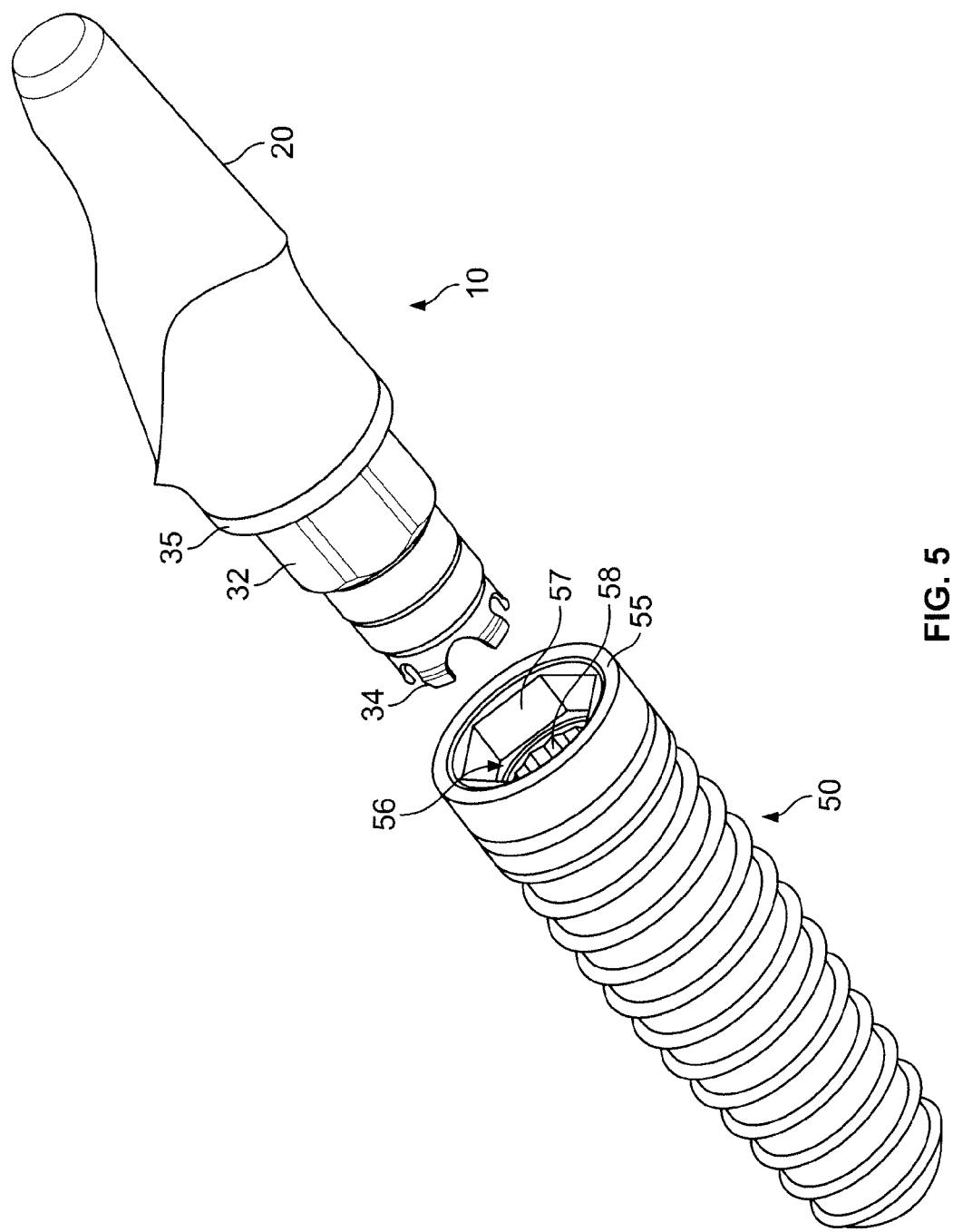
FIGS. 5 and 6 illustrate the mating relationship between the two-piece abutment and the implant.
Figure 6:
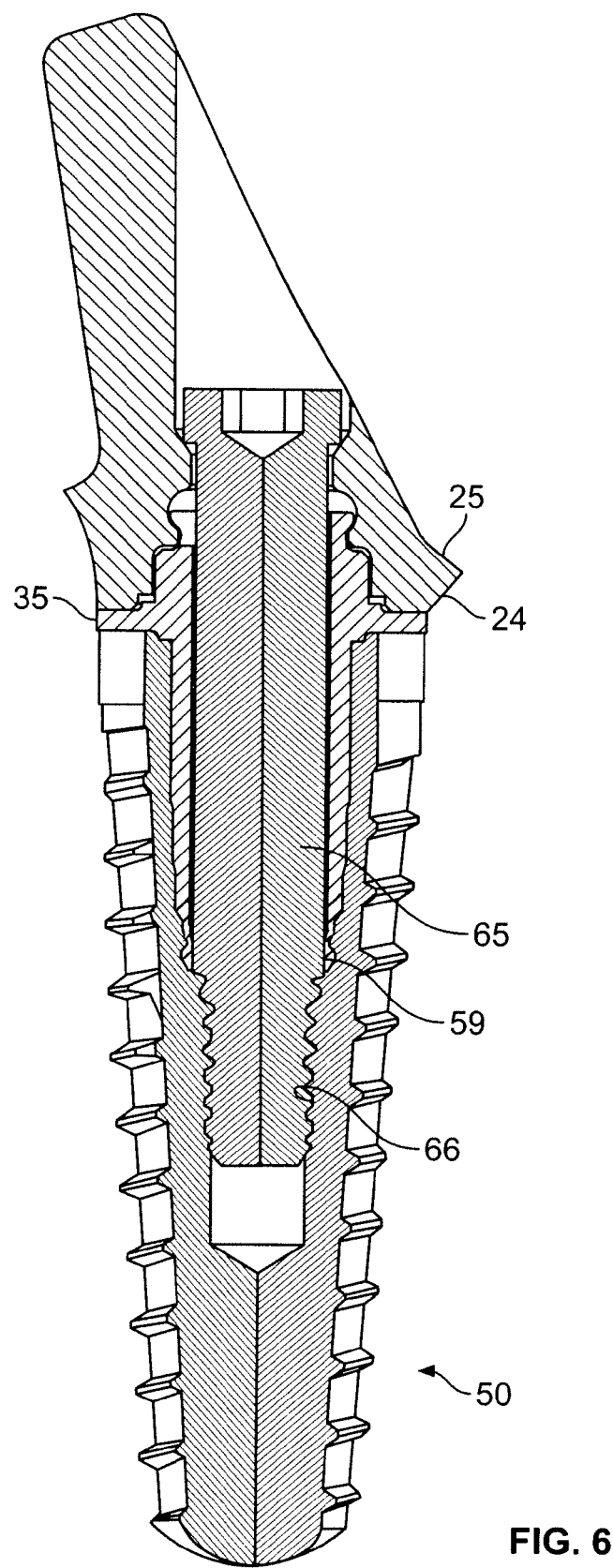

FIGS. 5 and 6 illustrate the two-piece abutment 10 mating with an implant 50. The implant 50 includes an upper surface 55 for engaging the table 35 of the insert 30, and an internal bore 56 having at least one anti-rotational feature. As shown, the implant 50 includes a first anti-rotational feature 57 and a second anti-rotational feature 58 just below the first anti-rotational feature 57. The non-round section 32 engages the first anti-rotational feature 57 on the implant 50. The second anti-rotational feature 58 may be used to drive the implant 50 into the bone or to mate with other types of components.

After the plurality of prongs 34 have snapped into a corresponding section 59 of the internal bore 56, the two-piece abutment 10 is fitted in the correct position within the implant 10. A screw 65 then mates with internal threads 66 located within the internal bore 56 of the implant 50 to hold the abutment 10 on the implant 50.

The insert 30 of the present invention is preferably made of titanium or titanium alloys, although it can be made of other biocompatible materials of sufficient properties to engage the dental implant 50 without deforming during usage. Accordingly, other exemplary materials include stainless steel, cobalt chromium alloys, gold alloys, ceramics (e.g., alumina, zirconium), and stronger plastics such as polyether-ether-ketone ("PEEK").

The prosthetic portion 20 is comprised of a biocompatible material having sufficient properties to support a prosthesis located on its support section 22. As such, the prosthetic portion 20 can be made of metal, such as titanium, titanium alloy, stainless steel, cobalt chromium alloys, and gold alloys. Additionally, the prosthetic portion 20 can be made of a ceramic material, such as alumina or zirconium, which, unlike the darker shaded metals, has a lighter coloring and providing better aesthetics. The prosthetic portion 20 can also be made of a polymeric material, such as PEEK, which may be especially useful for temporary abutments.

The present invention contemplates the use of a single type of insert 30 with a plurality of prosthetic portions 20 comprised of different materials. For example, a titanium insert 30 may be included within a single kit that includes a plurality of prosthetic portions 20 comprised of different materials, such as a titanium prosthetic portion 20 and a ceramic prosthetic portion 20.

The prosthetic portion 20 (and possibly a portion of the insert 30) may be treated with a biocompatible coating through a process, such as anodizing, deposition, sputtering, or plating, to render that component a color that is better disguised under the gingival tissue. For example, the prosthetic portion 20 can be treated with a gold-colored or pink-colored titanium anodizing process or a titanium nitride coating.

The insert 30 and/or prosthetic portion 20 can also be treated with a biocompatible treatment process, such as anodizing, deposition, sputtering, plating, or ion implantation, to impart anti-microbial properties. For example, the surfaces can be treated with anti-microbial silver particles (e.g., nano-scale particles) or an antibiotic delivered by controlled resorbable materials adhered to the surface. Because of the need for maintaining a clean and stable environment at the seams of any mating components in the mouth, the surfaces on the table 35 of the insert 30 and the corresponding lowermost surface of the prosthetic portion 20 may be particularly in need of a treatment in accordance with these processes, especially anti-microbial silver particles.

Furthermore, the insert 30 and/or prosthetic portion 20 can be treated with a biocompatible coating, such as anodizing, deposition, sputtering, plating, or ion implantation, to aid in the gingival tissue healing process. For example, the surfaces can be treated with collagen, hydroxyapatite (e.g., nano-scale crystalline particles of hydroxyapatite), growth factors, and/or proteins.

FIG. 7A illustrates a first set of angular positions 70 that is used with a two-piece abutment 10 having square-shaped non-round sections 26, 36 on the prosthetic portion 20 and on the insert 30. The anti-rotational feature 32, which is the hexagonally shaped boss section below the table 35 of the insert 30 (see FIG. 2), is also shown.

In position "a" of FIG. 7A, there is a certain angular orientation of one surface of the anti-rotational feature 32 of the insert 30 to one surface of the non-round section 26 of the prosthetic portion 20 (and, thus, for the upper support section 22 of the prosthetic portion 20). If the insert 30 is rotated clockwise 90 degrees (while keeping prosthetic portion 20 in the same position) such that surface 36a on the non-round section 36 of the insert 30 is engaged on the right surface of the non-round section 26 of the prosthetic portion 20, then position "b" between the insert 30 and the prosthetic portion 20 is established. Similarly, if the insert 30 is again rotated clockwise 90 degrees, such that the surface 36a is engaged on the bottom surface of the non-round section 26 of the prosthetic portion 20, then the position "c" between the insert 30 and the prosthetic portion 20 is established. Finally, if the insert 30 is again rotated clockwise 90 degrees, such that the surface 36a is engaged on the left surface of the non-round section 26 of the prosthetic portion 20, then position "d" between the insert 30 and the prosthetic portion is established.

Accordingly, as illustrated in first set of angular positions 70 in FIG. 7A, there are four possible relative positions between one surface of the anti-rotational feature 32 of the insert 30 and the upper support region 22 of the prosthetic portion 20. However, two sets of positions (a & c; b & d) are duplicates of each other. Considering that the hexagonal anti-rotational feature 32 provides six possible final positions on the implant 60, the overall two-piece abutment 10 can provide up to twelve different mounting positions on the implant 60 (2 positions at the insert 30/prosthetic portion 20 interface multiplied by 6 positions of the hexagonal anti-rotational feature 32). This is important when the support region 22 is asymmetrically arranged around a central axis of the prosthetic portion 20 to create an angled abutment on the implant 60.

FIG. 7B illustrates a second set of angular positions 80 wherein the non-round section 26' of the prosthetic portion 20 and the non-round section 36' of the insert 30 are modified to have an octagonal shape as opposed to a square shape. Following the analysis set forth to the first set of angular positions 70 in FIG. 7A, there are eight possible positions for inserting the insert 30 into the prosthetic portion 20. Accordingly, there are eight possible angular configurations of the prosthetic portion 20 relative to the insert 30 with four sets of positions (a & e; b & f; c & g, d & h) being duplicates of each other. Considering that the hexagonal anti-rotational feature 32 provides six different positions on the implant 60, the overall two-piece abutment 10 can provide up to twenty-four different mounting positions on the implant 60 (4 positions at the insert 30/prosthetic portion 20 interface multiplied by 6 positions of the hexagonal anti-rotational feature 32).

In summary, FIGS. 7A and 7B illustrate that the two-piece abutment 10 provides for multiple abutment positions on the implant 50 with less variations in component manufacturing that is required. Rather than machining a single-piece angled abutment with two different variations for the position of the underlying hexagonal socket to fit on the implant in 12 ways, a single prosthetic portion 20 and a single insert 30 can provide the same result if a square brooch is used for the non-round sections 26, 36. And if an octagonal broach is used for the non-round sections 26, 36, a single prosthetic portion 20 and a single insert 30 can provide the same result as four angled abutments, each with a different position of the underlying hexagonal socket.

Figure 8A:
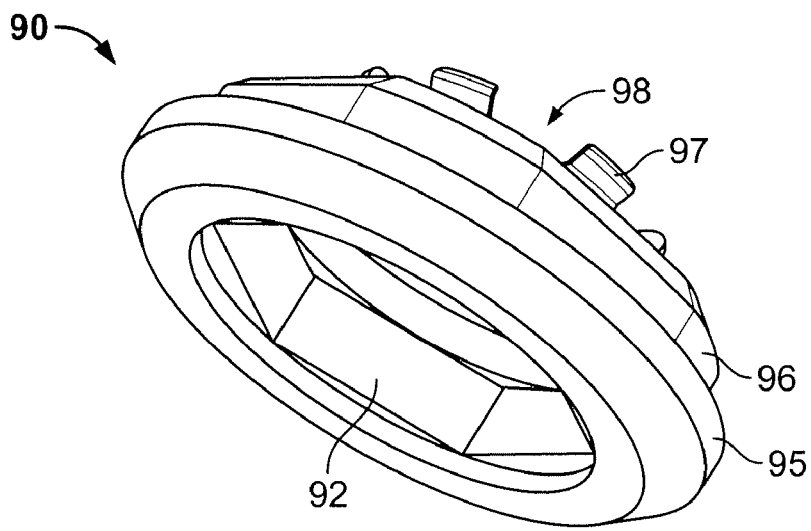
FIGS. 8A and 8B illustrate a two-piece abutment using the prosthetic portion of FIG. 3 and an alternative insert that is used with an implant having an external hexagonal anti-rotational feature.
Figure 8B:
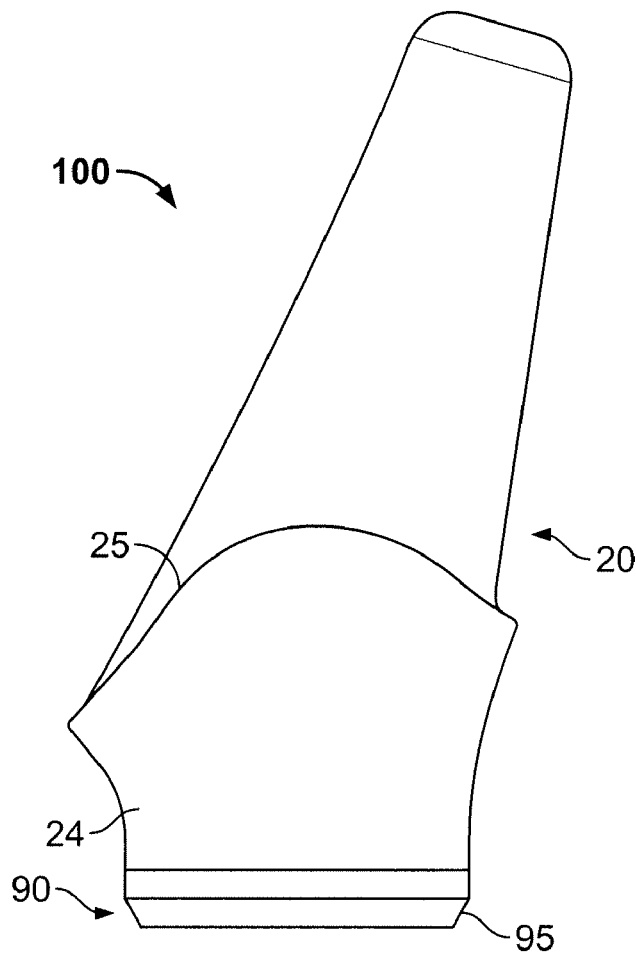
Figure 9:
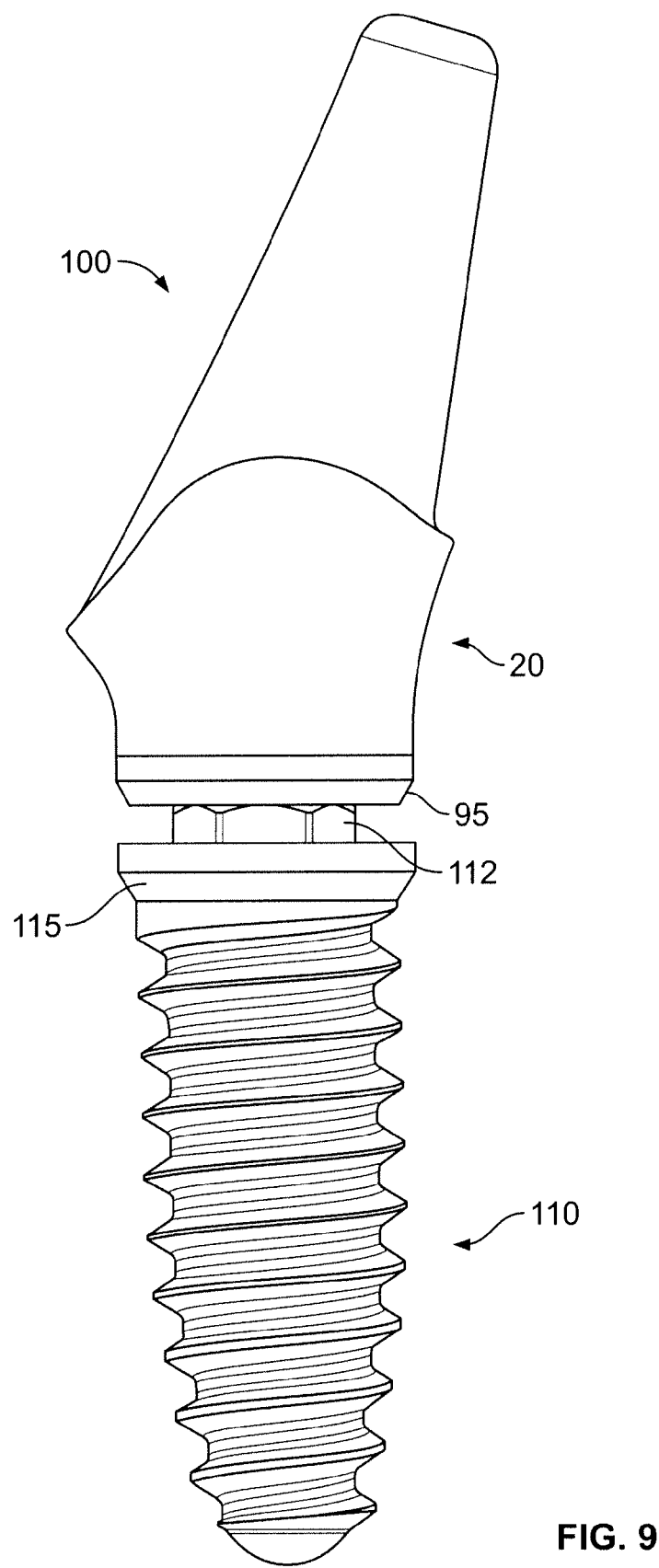
FIG. 9 illustrates the two-piece abutment of FIG. 8 on an implant having an external hexagonal anti-rotational feature.

FIGS. 8A and 8B illustrate an alternative insert 90 that can be used with the prosthetic portion 20. The insert 90 includes internal non-rotational feature 92 (e.g., a hexagonal socket) below a table 95. A non-round section 96 and the plurality of fingers 97 above the table 95 have the same configuration as the non-round section 36 and the plurality of fingers 37 of the insert 30 in FIG. 2. As such, the insert 90 can be used with the same prosthetic portion 20 to create a two-piece abutment 100 that is intended to mate with an implant 110 having a corresponding hexagonal boss 112 above the table 115, as shown best in FIG. 9. Additionally, inserts can be developed that include lower features for engagement with other types of mating features on implants, such as Morse tapers, or other non-round shapes.

Accordingly, the present invention contemplates a kit of components that includes a plurality of different inserts capable of mating with a plurality of different implants. Each of the inserts can be used with the same prosthetic portion 20. The kit also includes a plurality of different sizes and shapes of prosthetic portions 20 that mate with each type of insert, providing substantial variation for the resulting two-piece abutments.

It should be noted that the present invention contemplates a simple kit of components that can be used by the clinician for a temporary abutment prior to the placement of a permanent abutment on the implant. Often, such a temporary abutment may be placed on the implant after it has been installed with an "immediate loading" protocol. In this situation, the clinician would choose an insert 30 and an appropriately sized and shaped prosthetic portion that will receive temporary material, such as acrylic, to provide the patient with an aesthetically pleasing prosthetic tooth mounted on the implant. The clinician would use the snap-fit feature to attach the insert 30 to the selected prosthetic portion 20 prior to the placement on the implant for use as a temporary abutment.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims. For example, the present invention contemplates kits having the inserts and prosthetic portions of the same general configuration, but different sizes to accommodate differently sized implants.

What is claimed is:

1. An abutment for use with a dental implant, said dental implant having an internally threaded bore and a non-round fitting located at a gingival end portion thereof, said abutment comprising:
   a prosthetic portion adapted to support a prosthesis thereon, said prosthetic portion having a supragingival region for protruding beyond gingiva adjacent to said dental implant and a subgingival end, said prosthetic portion having a passageway extending therethrough, said passageway including an enlarged retention groove, a first non-round section, and a narrow shoulder;
   an insert extending into said passageway and engaging said subgingival end of said prosthetic portion, said insert including a second non-round section for non-rotationally mating with said first non-round section of said prosthetic portion, said insert having a central opening and an anti-rotational feature for engaging said non-round fitting of said dental implant, said insert including flexible retention fingers adjacent to said second non-round section that, upon insertion into said passageway, initially contract before reaching said enlarged retention groove and then expand outwardly into said enlarged retention groove to hold said insert onto said prosthetic portion; and
   a screw adapted to engage threads of said internally threaded bore in said implant and insertable through said passageway in said prosthetic portion and said central opening in said insert, said screw comprising a head and a threaded section, said head of said screw seating on said shoulder in said passageway.

2. The abutment of claim 1, wherein said first non-round section and said second non-round section are polygons having "n" sides, said anti-rotational feature being a polygonal fitting with "m" sides.

3. The abutment of claim 2, wherein said prosthetic portion is asymmetrically arranged around a central axis of said prosthetic portion such that said abutment is an angled abutment, said number "m" being different from said number "n", said insert being insertable into said prosthetic portion in one of a plurality of positions such that said asymmetrically arranged prosthetic portion can be at one of a plurality of angles with respect to one of said "m" sides on said polygonal fitting.

4. The abutment of claim 1, wherein said insert includes a lower protruding section having said anti-rotational feature.

5. The abutment of claim 4, wherein said lower protruding section includes a snap-fit section for engagement in a corresponding snap-fit receiving region of said dental implant.

6. The abutment of claim 1, wherein said insert includes an internal recess having said anti-rotational feature for mating with said non-round fitting on an external boss of said implant.

7. The abutment of claim 1, wherein said insert has a table that is substantially the same diameter as the upper interfacing surface of said dental implant.

8. A method of manufacturing a dental abutment for use on a dental implant in a patient's mouth, said dental abutment having a prosthetic portion and an insert including a plurality of resilient fingers, said method comprising:
   placing an upper segment of said insert into a passageway of said prosthetic portion;
   non-rotationally mating a first non-round section of said insert, that is adjacent to said plurality of resilient fingers, with a second non-round section in said passageway of said prosthetic portion;
   expanding said plurality of resilient fingers on said insert; and
   in response to said insert being placed a certain distance within said passageway, snap-fitting said insert into a final position with said prosthetic portion.

9. The method of claim 8, wherein said first non-round section and said second non-round section are polygons having "n" sides, said insert has a lower section having an anti-rotational feature with "m" sides for non-rotationally mating with a corresponding feature on said implant.

10. The method of claim 9, wherein said prosthetic portion is asymmetrically arranged around a central axis of said prosthetic portion such that said abutment is an angled abutment, said number "m" being different from said number "n", said insert being insertable into said prosthetic portion in one of a plurality of positions such that said asymmetrically arranged prosthetic portion can be at one of a plurality of angles with respect to one of said "m" sides on said anti-rotational feature.

11. The method of claim 10, wherein said number "m" is six and said number "n" is four, said asymmetrically arranged prosthetic portion can be at one of twelve angles with respect to one of said six sides on said corresponding anti-rotational feature of said implant.

12. The method of claim 10, wherein said number "m" is six and said number "n" is eight, said asymmetrically arranged prosthetic portion can be at one of twenty-four angles with respect to one of said six sides on said corresponding anti-rotational feature of said implant.

13. The method of claim 10, wherein said asymmetrically arranged prosthetic portion can be at one of at least ten different angles with respect to one of said six sides on said corresponding anti-rotational feature of said implant.

14. An abutment for use with a dental implant, said dental implant having an internally threaded bore and a non-round fitting located at a gingival end portion thereof, said abutment comprising:
- a prosthetic portion adapted to support a prosthesis thereon, said prosthetic portion having a subgingival end and a supragingival region for protruding beyond gingiva adjacent to said dental implant, said supragingival region being asymmetrically arranged around a central axis of said prosthetic portion such that said abutment can function as an angled abutment, said prosthetic portion having a passageway extending therethrough, said passageway including an enlarged retention groove and non-round section having "n" number of sides;
- an insert extending into said passageway and engaging said subgingival end of said prosthetic portion, said insert having a central opening and an anti-rotational feature with "m" sides for engaging said non-round fitting of said dental implant, said insert including flexible retention fingers that, upon insertion into said passageway, initially contract before reaching said enlarged retention groove and then expand outwardly into said enlarged retention groove to hold said insert onto said prosthetic portion, said insert including a corresponding non-round section with "n" number of sides for mating with said non-round section of said passageway; and
- wherein said insert is insertable into said prosthetic portion in one of a plurality of positions such that said asymmetrically arranged supragingival region can be at one of a plurality of angles with respect to one of said "m" sides on said anti-rotational feature.

15. The abutment of claim 14, wherein said anti-rotational feature is a polygonal protruding boss.

16. The abutment of claim 14, wherein said insert and said prosthetic portion are made of dissimilar materials.

17. An abutment for use with a dental implant, the dental implant having an internally threaded bore and a non-round fitting located at a gingival end portion thereof, the abutment comprising:
- a prosthetic portion adapted to support a prosthesis thereon, the prosthetic portion having a supragingival region for protruding beyond gingiva adjacent to the dental implant, the prosthetic portion having a passageway extending therethrough and including a first non-round section;
- an insert including a second non-round section for non-rotationally engaging the first non-round section of the prosthetic portion, the insert having a central opening and an anti-rotational feature for engaging the non-round fitting of the dental implant, the insert including flexible retention fingers adjacent to the second non-round section that, upon insertion into the passageway, initially contract to hold the insert onto the prosthetic portion.

18. The abutment of claim 17, further comprising a screw adapted to engage threads of the internally threaded bore in the implant and insertable through the passageway in the prosthetic portion and the central opening in the insert, the screw comprising a head and a threaded section, the head of the screw seating on a shoulder in the passageway.

19. The abutment of claim 17, wherein the first non-round section and the second non-round section are polygons having "n" sides, the anti-rotational feature being a polygonal fitting with "m" sides.

20. The abutment of claim 19, wherein the prosthetic portion is asymmetrically arranged around a central axis of the prosthetic portion such that the abutment is an angled abutment, the number "m" being different from the number "n," the insert being insertable into the prosthetic portion in one of a plurality of positions such that the asymmetrically arranged prosthetic portion can be at one of a plurality of angles with respect to one of the "m" sides on the polygonal fitting.

* * * * *